United States Patent
Liu et al.

(10) Patent No.: US 7,412,026 B2
(45) Date of Patent: Aug. 12, 2008

(54) PHASE-CONTRAST X-RAY IMAGING SYSTEMS AND METHODS

(75) Inventors: Hong Liu, Norman, OK (US); Xizeng Wu, Birmingham, AL (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 428 days.

(21) Appl. No.: 11/171,006

(22) Filed: Jun. 29, 2005

(65) Prior Publication Data

US 2006/0039532 A1    Feb. 23, 2006

Related U.S. Application Data

(60) Provisional application No. 60/585,137, filed on Jul. 2, 2004.

(51) Int. Cl.
*G01N 23/04* (2006.01)
*G21K 5/08* (2006.01)
*H05G 1/64* (2006.01)

(52) U.S. Cl. .............. 378/62; 378/68; 378/98.8

(58) Field of Classification Search .......... 378/4, 378/5, 16, 19, 37, 62, 108, 210, 68, 98.8
See application file for complete search history.

(56) References Cited

U.S. PATENT DOCUMENTS

| | | | |
|---|---|---|---|
| 2003/0072406 A1* | 4/2003 | Yang | 378/4 |
| 2004/0264627 A1* | 12/2004 | Besson | 378/5 |
| 2005/0058259 A1* | 3/2005 | Vija et al. | 378/210 |
| 2005/0226376 A1* | 10/2005 | Yun et al. | 378/62 |
| 2006/0015952 A1* | 1/2006 | Filvaroff | 800/10 |
| 2006/0109949 A1* | 5/2006 | Tkaczyk et al. | 378/4 |

OTHER PUBLICATIONS

Xizeng Wu and Hong Liu, "A general theoretical formalism for X-ray phase contrast imaging", Journal of X-ray Science and Technology 11 (2003), IOS Press, pp. 33-42.

Xizeng Wu and Hong Liu, "An experimental method of determining relative phase-contrast factor for x-ray imaging systems", Med. Phys. 31 (5), May 2004; 2004 Am. Assoc. Phys. Med., pp. 997-1002.

* cited by examiner

*Primary Examiner*—Irakli Kiknadze
(74) *Attorney, Agent, or Firm*—Dunlap Codding, P.C.

(57) ABSTRACT

The present invention relates systems and methods for phase-contrast x-ray imaging of an object. In one embodiment, the system includes an x-ray source, a detector, and an object-map generator. The x-ray source transmits x-rays, and the detector is positioned so as to receive at least a portion of the x-rays transmitted by the x-ray source and output an image signal indicative of an intensity measurement of the x-rays received. The object is positioned between the x-ray source and the detector. The detector is then used to acquire intensity measurements at two different positions and output the same to the object-map generator. The object-map generator then utilizes the image signals of the detector, along with algorithms, including phase-retrieval algorithms to generate an attenuation-map and a phase-map for the object. The present invention also include systems and methods utilizing a dual-detector arrangement, a multi-source arrangement, and a mosaic source-detector arrangement.

29 Claims, 5 Drawing Sheets

| Source to Object $R_1$ (m) | 0.60 | 0.50 | 0.60 |
|---|---|---|---|
| Object-detector $R_2$ (m) | 0.40 | 0.30 | 0.40 |
| Source to detector distance (m) | 1.00 | 0.80 | 1.00 |
| Magnification $(R_1+R_2)/R_1$ | 1.67 | 1.60 | 1.67 |
| Target frequency (lp/mm) | 20.00 | 20.00 | 20.00 |
| Max. pixel width at detector (mm) | 0.04 | 0.04 | 0.04 |
| X-ray focal spot size (mm) | 0.025 | 0.025 | 0.025 |
| X-ray kVp | 30 | 25 | 25 |
| Tube Target/filter | Mo/Mo | Mo/Mo | Mo/Mo |
| HVL (mm) Al | 0.382 | 0.32 | 0.32 |
| Breast-Lesion attenuation –SNR | 135.52 | 170.94 | 170.94 |
| Entrance Skin Exposure (R) | 1.220 | 1.897 | 2.058 |
| Patient absorbed Dose (mRad) | 198.15 | 254.45 | 276.10 |
| Relative phase-contrast factor at target frequency | 1.95E-02 | 1.83E-02 | 2.30E-02 |
| Exposure time @25 mA (sec) | 3.63 | 6.27 | 9.80 |

Table 1

*Fig. 4A*

| Source to Object $R_1$ (m) | 0.60 | 0.5 | 0.60 | 0.50 | 0.4 |
|---|---|---|---|---|---|
| Object-detector $R_2$ (m) | 0.40 | 0.5 | 0.40 | 0.30 | 0.6 |
| Source to detector distance (m) | 1.00 | 1.00 | 1.00 | 0.80 | 1.00 |
| Magnification $(R_1+R_2)/R_1$ | 1.67 | 2.00 | 1.67 | 1.60 | 2.50 |
| Digital detector pixel pitch (mm) | 0.07 | 0.07 | 0.07 | 0.07 | 0.07 |
| Target frequency (lp/mm) | 11.9 | 14.3 | 11.9 | 11.4 | 17.9 |
| Focal spot size (mm) | 0.025 | 0.025 | 0.025 | 0.025 | 0.025 |
| X-ray kVp | 30 | 30 | 25 | 25 | 30 |
| Tube Target/filter | Mo/Mo | Mo/Mo | Mo/Mo | Mo/Mo | Mo/Mo |
| HVL (mm) Al | 0.382 | 0.382 | 0.32 | 0.32 | 0.382 |
| Breast-Lesion attenuation. –SNR | 135.52 | 135.5 | 170.94 | 170.94 | 135.5 |
| Entrance Skin Exposure (R) | 1.220 | 1.757 | 2.058 | 1.897 | 2.745 |
| Patient absorbed Dose (mRad) | 198.15 | 285.3 | 276.10 | 254.45 | 445.8 |
| Relative phase-contrast factor at target fequency | 7.53E-03 | 1.06E-02 | 8.90E-03 | 6.47E-03 | 1.39E-02 |
| Exposure time @25 mA (sec) | 3.63 | 3.63 | 9.80 | 6.27 | 3.63 |

Table 2

PHASE-CONTRAST X-RAY IMAGING SYSTEMS AND METHODS

CROSS-REFERENCE TO RELATED APPLICATIONS

The present application claims priority to the provisional patent application identified by the U.S. Ser. No. 60/585,137, which was filed on Jul. 2, 2004, the entire content of which is hereby expressly incorporated herein by reference.

STATEMENT REGARDING FEDERALLY SPONSORED RESEARCH AND DEVELOPMENT

Not Applicable.

SUMMARY OF THE INVENTION

In general, diagnostic x-ray imaging of an object, such as a human organ, relies on the small differences in linear attenuation coefficients between different tissues within the object to produce a projection image. However, as a partially coherent x-ray beam propagates through the object, additional information relating to phase and phase contrast can be observed due to the variation of the x-ray refractive index between different tissues and boundaries within the object. In the present invention for x-ray imaging, the phase contrast information is also recorded, and with the appropriate geometry, is used to enhance tissue boundaries and interfaces in a radiographic image. The enhancement process is also referred to as "edge enhancement". Further, since the different tissues within the object will also have differences in attenuation coefficients, the overall effect of phase contrast imaging technique of the present invention is to increase contrast sensitivity.

The present invention offers improved contrast sensitivity utilizing phase contrast in x-ray imaging. The primary object of the present invention is to provide systems and methods for phase-contrast imaging based on: (1) a novel application of a field-emission x-ray source in phase contrast imaging; (2) a novel method to guide the design of in-line phase contrast imaging systems and evaluate the performance of the phase and phase contrast x-ray imaging; (3) a novel multi-source architecture to acquire phase and phase contrast images; (4) an innovative scatter rejection method and a one-detector, two-step acquisition technique; (5) a dual-detector technique to acquire phase and attenuation images; and (6) a novel algorithm to retrieve phase information and reconstruct both phase and attenuation images. A further goal the present invention is to balance the relationships between detector geometry, detector resolution, x-ray source size and radiation output, and patient exposure/dose during phase-contrast imaging.

The present invention can be applied widely in diagnostic radiography procedures. It can be applied in many human and non-human imaging applications, including medical imaging (e.g., mammography and radiography) and industrial x-ray applications. It can also be effectively and economically fitted in current diagnostic radiography rooms and operated at currently preferred patient radiation dose levels, but with significantly improved diagnostic sensitivity and specificity. As such, clinical feasibility is another feature of the present invention.

These various objects and features, together with other objects and features of novelty which characterize the invention, are discussed and illustrated in further detail herein, and are pointed out with particularity in the claims.

DETAILED DESCRIPTION OF THE INVENTION

In general, the systems and methods of the present invention relate to x-ray phase-contrast imaging of an object, such as for example human organs. In one preferred embodiment, the present invention is specifically adapted for application in mammography technology for the imaging of human breast tissue. However, one of ordinary skill in the art would understand that the present invention is not limited to only mammography applications, and can be used for any imaging application. For example, the present invention can be used for medical diagnostics, forensic analysis, industrial inspections, or any other human or non-human examination.

Figure 1:
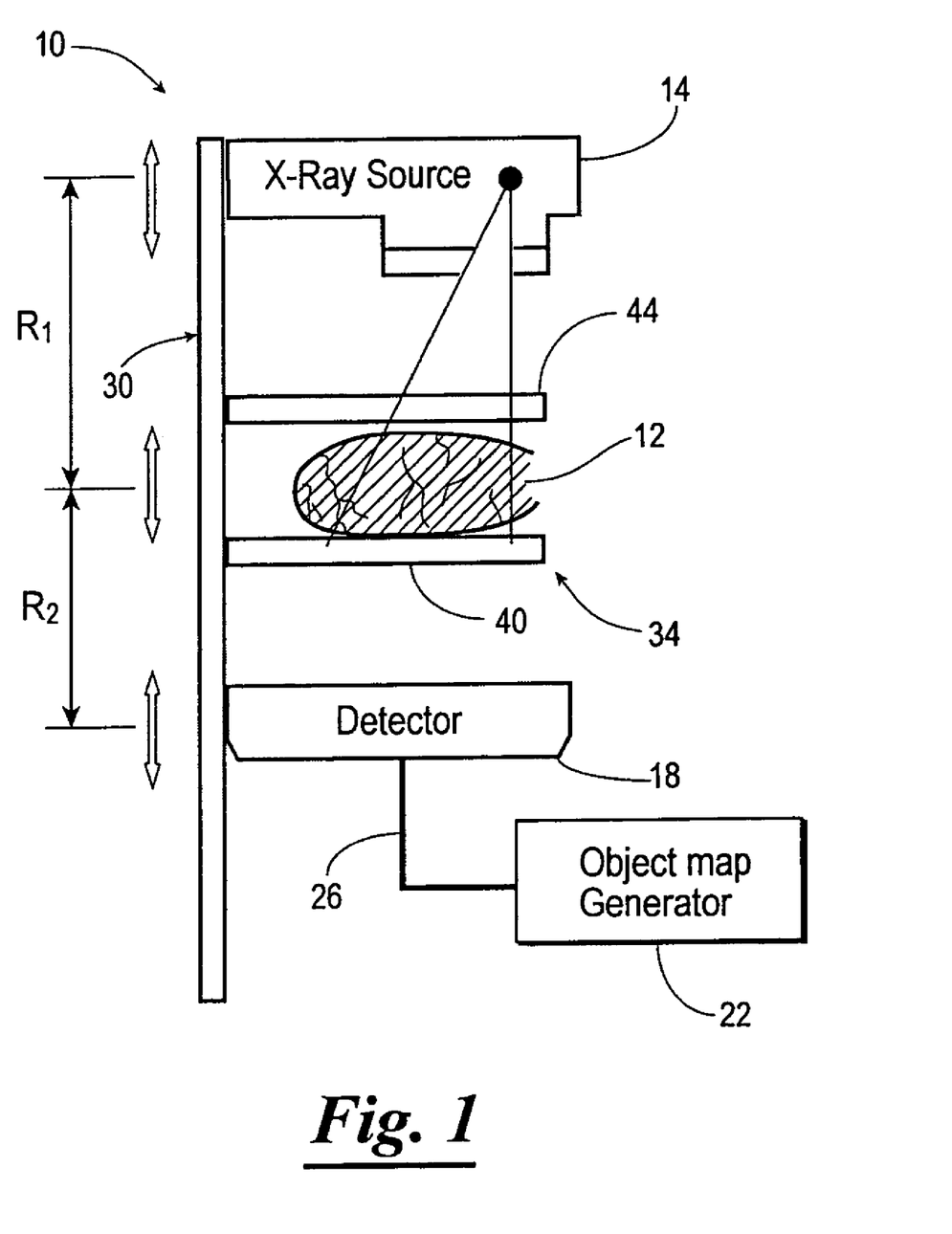
FIG. 1 is a schematic of one embodiment of a system for phase-contrast x-ray imaging of an object, which is constructed in accordance with the present invention.

Referring now to the figures and in particular to FIG. 1, shown therein and designated by a reference numeral 10 is a system for phase-contrast x-ray imaging of an object 12, which is constructed in accordance with the present invention. The system 10 includes an x-ray source 14 for transmitting x-rays, and a detector 18 positioned so as to receive at least a portion of the x-rays transmitted by the x-ray source 14 and output an image signal indicative of the intensity of the x-rays received.

The x-ray source 14 and the detector 18 are space apart a distance sufficient to allow the object 12 to be positioned therebetween for imaging. In one embodiment, as shown for example in FIG. 1, the x-ray source 14 and the detector 18 are arranged vertically such that the x-ray source 14 is positioned on top of the object 12 (e.g. a body part of a patient), while the detector 18 is positioned beneath the object 12 so as to provide an air-gap sufficient for phase contrast imaging (e.g., for a clinical application). Also, to insure accuracy, the x-ray source 14, the detector 18, and the object 12 are held substantially stationary during the imaging process.

When the object 12 is placed between the x-ray source 14 and the detector 18 (where $R_1$ is the distance between the x-ray source 14 and the object 12, and $R_2$ is the distance between the object 12 and the detector 18), the object 12 interferes with the x-rays transmitted by the x-ray source 12 and received by the detector 18. The object 12 causes attenuation of the x-rays due to small differences in linear attenuation coefficients between different materials or structures (e.g., tissues and lesions) within the object 12. Also, as a partially coherent x-ray beam propagates through the object, additional information relating to phase and phase contrast can also be observed due to the variation of the x-ray refractive index between different materials and boundaries (e.g. tissue-lesion boundaries) within the object. In other words, the object 12 also causes a phase change in the x-rays.

Both the attenuation and phase change caused by the object 12 will affect the intensity of the x-rays received by the detector 18. Therefore, it is possible to retrieve from the image signals of the detector 18 an attenuation-map, or an x-ray projection image based on attenuation information, and a phase-map, or an x-ray projection image based on phase contrast information, for the object 12.

To generate the attenuation-map and the phase-map of the object 12, the system 10 further includes an object-map generator 22 which receives the outputted image signals of the detector 18 via a line 26. In general, the object-map generator 22 is a computer system operating a software program which utilizes algorithms, including phase-retrieval algorithms (which are discussed in further detail below), to reconstruct or generate the attenuation-map and the phase-map of the object 12.

In one embodiment, the object-map generator 22 utilizes intensity measurements acquired by the detector 18 at two different $R_2$ positions. Preferably, the two different $R_2$ positions are at about $R_2=0$ and $R_2>0$. In general, one detector reading is utilized to determine attenuation, and the other detector reading is utilized to determine phase-contrast (which leads to enhanced object boundary and interface information). Because the x-ray phase differences between the object boundaries (e.g. those between tissue and lesions) are hundreds times larger than conventional attenuation contrast images, the object phase-map of the present invention provides an improved, sensitive and quantitative way for object imaging.

Once generated by the object-map generator 22, the attenuation-map and/or the phase-map can then be outputted, e.g., to an output device (not shown) of the object-map generator 22 (such as a monitor or printer), so that the attenuation-map and/or the phase-map can be displayed and/or further analyzed. In one embodiment, the attenuation-map and the phase-map are outputted as digital images, and can be displayed in any pixel format and bit-depth. Further, the information within the attenuation-map and the phase-map can be combined to generate an object-map for the object 12, which can also be outputted to the output device.

In general, the algorithms utilized to generate the attenuation-map and the phase-map of the present invention are derived using a theory of in-line holography for objects with attenuation, which is based on the Fresnel diffraction analysis of x-rays.

One theoretical model which accounts for the interplay of attenuation, phase-change and image intensity is given by the formula:

$$\tilde{I}(u,z) \approx \delta(u) - \cos(\pi\lambda z u^2) M(u) + 2\Phi(u)\sin(\pi\lambda z u^2) \quad (1)$$

where $\tilde{I}(u,z)$, $\Phi(u)$ and $M(u)$ are the Fourier Transforms (FTs) of image intensity at z, the projected phase of the object 12, and the projected attenuation of the object 12, respectively. However, there are several limitations of Eq. (1) which impede its application for clinical imaging.

First of all, Eq. (1) was derived under the assumption of $|\phi(x)| \ll 1$ and $\mu(x) \ll 1$, and thus the results using this assumption are valid only for phase imaging of weakly attenuating and weak phase objects of very thin tissue samples. These assumptions will be grossly violated for larger applications, such as for example mammography. Therefore, the phase-contrast image intensity formula of Eq. (1) will be invalid for phase-contrast mammography. Second, Eq. (1) was derived by assuming only a plane wave incident x-ray generated from synchrotron radiation sources. Third, in mammography, x-rays from an x-ray tube are bundles of spherical waves. The geometrical magnification involved in clinical imaging will affect the wavefront curvature as well, in addition to the phase change from the imaged object 12. Finally, Eq. (1) was derived assuming that the image intensity varies in one dimension only, and in mammography, image intensity varies in two dimensions.

To overcome the above-mentioned limitations of Eq. (1) for clinical imaging applications, another theoretical model can be used to model the interplay of tissue attenuation, phase and image intensity, as defined by the following equation:

$$\tilde{I}(u,v) = \frac{I_{10}}{M^2} \left\{ \cos\left(\frac{\pi\lambda R_2(u^2+v^2)}{M}\right) FT(A_o^2) + 2\sin\left(\frac{\pi\lambda R_2(u^2+v^2)}{M}\right) FT(A_o^2 \phi) \right\} \quad (2)$$

where $I(u, v)$ is the Fourier transform of the image intensity measured by the detector 18, $I_{10}$ is the x-ray incident intensity upon the object 12, u and v are the spatial frequency in x- and y-direction, respectively, $\lambda$ is the wavelength, and M is the magnification factor and equals $(R_1+R_2)/R_1$. $A_0$ and $\phi$ are the amplitude and phase, respectively, of the object transmission function $q(x, y)$, which is given by the equation:

$$q(x,y) = A_0(x,y) \exp[i\phi(x,y)] \quad (3)$$

FT($A_0^2$) denotes the Fourier transform of $A_0^2(\eta,\xi)$, where:

$$FT(A_o^2) \equiv \int_{-\infty}^{\infty} A_0^2(\eta,\xi) e^{i2\pi(\eta u+\xi v)} d\eta d\xi, \quad (4)$$

and FT($A_0^2\phi$) is the Fourier transform of $A_0^2(\eta,\xi)\phi(\eta,\xi)$, where:

$$FT(A_0^2\phi) \equiv \int_{-\infty}^{\infty} A_o^2(\eta,\xi)\phi(\eta,\xi) e^{i2\pi(\eta u+\xi v)} d\eta d\xi. \quad (5)$$

As defined before, $R_2$ is the distance from the object plane to detector plane, and M is the magnification factor, which is equal to $(R_1+R_2)/R_1$ It can be seen from the general formula of Eq. (2) that it covers Eq. (1) as a special case for a one-dimensional object with weak attenuation and phase ($|\phi(x)|\ll 1$ and $\mu(x)\ll 1$) and illuminated by a plane wave incident x-ray (M=1).

Moreover, Eq. (2) suggests a general strategy for attenuation/phase retrieval as follows. From an image acquired at $R_2=0$, one obtains the Fourier transform of tissue attenuation $A_0^2$ from:

$$FT(A_o^2) = \frac{M^2}{I_{10}} \tilde{I}(u,v; R_2=0) \quad (6)$$

and then tissue projected attenuation $A_0^2(\eta,\xi)$ can be found from (FT($A_0^2$)) by an inverse FT. The attenuation-map determination is similar to that used in current imaging techniques, such as a conventional mammogram acquired in the contact mode (as derived from the first reading of the detector 18.

One then obtains FT($A_0^2\phi$) from the information acquired at $R_2>0$ (as derived from the second reading of the digital detector 18) and the found FT($A_0^2$) by using following equation:

$$FT(A_o^2\phi) = \left\{\frac{M^2}{I_{10}}\tilde{I}(u,v) - \cos\left(\frac{\pi\lambda R_2(u^2+v^2)}{M}\right) FT(A_o^2)\right\} / \left\{2\sin\left(\frac{\pi\lambda R_2(u^2+v^2)}{M}\right)\right\} \quad (7)$$

In a mammography application by way of example, the average x-ray photon energy is about 20 keV, the maximal spatial resolution is about 20 lp/mm or less, and $R_2/M<1$ m, hence $\lambda R_2(u^2+v^2)/M\ll 1$. Hence Eq. (7) may be reduced to:

$$FT(A_o^2\phi) = \left(\frac{M^2}{I_{10}}\tilde{I}(u,v) - FT(A_o^2)\right) / \left(\frac{2\pi\lambda R_2(u^2+v^2)}{M}\right) \quad (8)$$

Once FT($A_0^2\phi$) is found, one can further take the Fourier-transform FT($A_0^2\phi$) to get $A_0^2\phi$ and the phase-map $\phi(\eta,\xi)$ results as $A_0^2\phi/A_0^2$.

With a polychromatic x-ray source (such as for example a Mo/Mo micro-focus field emission x-ray tube), the effects of limited chromatic coherence is also to be considered. Note that Eq. (8) is wavelength dependent. Integrating Eq. (6) and Eq. (8) over the incident x-ray spectrum and using the following equations, the image intensity measured at $R_2=0$ again gives the tissue attenuation information to the incident polychromatic x-ray:

$$FT(A_{SA}^2) = \frac{M^2}{I_{10}}\tilde{I}(u,v; R_2=0) \quad (9)$$

where $A_{SA}^2(\eta,\xi)$ is the tissue attenuation-map for a normalized spectrum $w(\lambda)$ of the incident x-ray beam and is given by the formula:

$$A_{SA}^2(\eta,\xi) = \int A_0^2(\eta,\xi;\lambda) w(\lambda) d\lambda \quad (10)$$

where $A_0^2(\eta,\xi;\lambda)$ is the object attenuation for x-ray of wavelength $\lambda$. From an image signal acquired at $R_2=0$, one obtains the Fourier transform of the object attenuation $A_{SA}^2(\eta,\xi)$ from Eq. (9), and the object attenuation map $A_{SA}^2(\eta,\xi)$ results from inverse FT of Eq. (10).

To acquire the second reading from the detector 18, the detector 18 is moved to a distance of from the first position, i.e., $R_2>0$. The following equation relating the phase-map $\phi(\eta,\xi)$ to the image intensity measured at R2>0 is used:

$$FT(A_{SA}^2 \phi \langle \lambda^2 \rangle / \langle \lambda \rangle) = M\left[\frac{M^2}{I_{10}}\tilde{I}(u,v;R_2) - FT(A_{SA}^2)\right] / [2\pi R_2(u^2+v^2)] \quad (11)$$

where $\langle\lambda^2\rangle$ and $\langle\lambda\rangle$ denote the averages of $\lambda^2$ and $\lambda$ over the exiting x-ray spectrum, respectively. Fourier-transforming FT($A_{SA}^2\phi\langle\lambda^2\rangle/\langle\lambda\rangle$) and using the found $A_{SA}^2$, a map of $(\langle\lambda^2\rangle/\langle\lambda\rangle)\phi(\eta,\xi)$ can be reconstructed in gray scale. Note that the ratio of $\langle\lambda^2\rangle/\langle\lambda\rangle$ is actually a constant across a compressed object 12 (e.g., a human breast), thus a map would represent a map of phase $\phi(\eta,\xi)$ in gray scale.

In another embodiment, the phase map of the present invention can be generated in a similar manner using the formula:

$$\tilde{I}\left(\frac{\vec{u}}{M}; R_1+R_2\right) = I_{in}\tilde{\mu}_{in}\left(\frac{\lambda R_2 \vec{u}}{M}\right) OTF_{det}\left(\frac{\vec{u}}{M}\right)$$
$$\left\{\left(\hat{F}(A_o^2) - i\frac{\lambda R_2}{M}\vec{u}\cdot\hat{F}(\phi\nabla A_o^2)\right) + 2\frac{\pi\lambda R_2 \vec{u}^2}{M}\hat{F}(A_o^2\phi)\right\} \quad (12)$$

where $\tilde{I}(\vec{u};R_1+R_2)$ is the Fourier transform of the phase-contrast image intensity measured by the detector 18; $A_0^2$ denotes the attenuation map, and $\phi$ denotes the phase map. Note that the symbol $\hat{F}(\cdot)$ denotes the 2-D Fourier transform and $I_{in}$ is the intensity of the incident x-ray upon the object 12, $\vec{u}$ is the spatial frequency vector, and $\lambda$ is the wavelength. Again, the distance from the x-ray source 14 to the plane of the imaged object 12 is denoted as R1, and the distance from plane of the object 12 to the plane of the detector 16 is denoted as R2. Also, the geometric magnification factor M is equal to (R1+R2)/R1. The spatial coherence effects are accounted for by the formula $\mu_{in}(\lambda R_2 \vec{u}/M)$, which is referred to herein by the Applicants as the reduced complex degree of coherence of the entrance x-ray wave-field. The reduced complex degree of coherence is defined as the entrance wave complex coherence degree $\mu_{in}(\vec{s}_1, \vec{s}_2)$ with the overall phase factor removed and $\vec{s}_2 - \vec{s}_1 = \lambda R_2 \vec{u}/M$. The $\text{OTF}_{det}(\vec{u})$ is the spatial frequency response of the detector 18 at $\vec{u}$.

In designing the various physical components of the system 10, an initial consideration is coherence of the x-ray source 14 of the system 10. Theoretically, an x-ray source can be assumed to be a coherent monochromatic source. In reality however, x-ray sources are partially coherent or non-coherent. From the formula:

$$\tilde{I}(u, v) = \frac{I_{10}}{M^2}\left[FT(A_o^2) + \left(\frac{2\pi\lambda R_2(u^2 + v^2)}{M}\right)FT(A_o^2\phi)\right] \quad (13)$$

it can be seen that the phase-contrast term $\{\pi\lambda R_2(u^2+v^2)/M\}FT(A_o^2\phi)$ is not a oscillating function of wavelength. Hence, the contribution from different wavelengths cannot be destructive against each other. Therefore polychromatic x-rays, generated from an x-ray tube for example, can be used for phase-imaging in accordance with the present invention. Although, it should be understood that the x-ray spectrum does play a significant role in phase-contrast visibility.

While the temporal coherence of the x-rays produced by the x-ray source 14 is not critical for in-line phase-contrast imaging, the spatial coherence is critical. For example, if the x-ray source 14 includes an x-ray tube with a focal spot of size s, the diffraction waves generated by the object 12 from the individual spherical waves emitted by different points of the focal spot could destruct the interference effects, and the diffraction patterns could blur each other.

The spatial coherence of the x-ray source 14 can be characterized by its coherence width. The coherence width is the maximum distance between two projection points for which interference effects can be observed. The coherence width $L_{coh}$ for a monochromatic x-ray source with a focal spot of size s is:

$$L_{coh} = 2\lambda R_1/s \quad (14)$$

The lowest spatial frequency at which the sine-factor of phase-contrast is maximal is equal to $1/L_{coh}$. Therefore, the larger the $L_{coh}$ is, the better the phase-contrast transfer. For example, consider a 20 keV x-ray beam from the x-ray source 14 having a focal spot size of 1 µm, and an $R_1$ of 0.6 m, then the lowest $1/L_{coh}$ equals 13.44 lp/mm (which is in the resolution range of current mammography detectors). Thus, the phase-contrast is optimally transferred if a very bright x-ray source of about 1 µm-size were available. Unfortunately, to Applicants' knowledge, this kind of performance is out of the reach of the current x-ray tube technology. A smaller $L_{coh}$ means less phase-contrast visibility. For a polychromatic source, the temporal and spatial coherence effects become more complicated and cannot characterized simply by $L_{coh}$. Moreover, the imaged object 12 itself will affect the x-ray wave propagation and its coherence properties.

Another proposed measure of coherence known as the relative phase-contrast factor (RPF) provides a quantitative measure of phase-contrast visibility and can be also used to guide the designs of the system 10 in accordance with the present invention. The RPF, is given by the formula:

$$RPF(u, v) = \frac{c^2 h^2}{I}\left[\int \frac{\pi R_2(u^2 + v^2)}{ME^2}S_{Exit}(E)dE\right] \cdot \quad (15)$$

$$\sin c[\pi u(M-1)s/M] \cdot \sin c[\pi v(M-1)s/M]$$

where h is the Planck constant, c is the speed of light, $S_{Exit}(E)$ is the normalized spectrum of the average exiting beam (which represents the beam hardening effects on phase-contrast imaging), and s is the size of the focal spot of the tube. Also, I is a normalization factor that accounts for the dimension of the 2-D Fourier transform detected intensity (I=0.1 nm was assumed in the simulations described herein). The RPF (u, v) represents a quantitative measure of coherence and the visibility of phase-contrast at spatial frequency (u, v). It should be understood that RPF is not a percentage contrast; but rather it is a figure of merit in evaluating the capability of phase contrast transfer in x-ray imaging. The larger the RPF (u, v) is, the more the phase-contrast manifests in a recorded image.

It has been demonstrated based on computer simulation and experimental results using a lamb liver specimen that an RPF in the range of about 0.008 to about 0.02 at about 20 LP/mm is practically achievable, and it improves feature visibility significantly as compared to images recorded without phase contrast. The results of the simulation are summarized in the graphs shown in FIGS. 2 and 3. In the simulation, the RPF was calculated as the x-ray spectrum-weighted sum at the target frequency $U_{ob-max}$=20 lp/mm. Considering the current availability of an Mo/Mo target/filter assembly, a Mo/Mo x-ray spectra was used in the simulation by way of example. The phase-contrast visibility at a 20 lp/mm spatial frequency was simulated as a function of system design parameters, including $R_1$, $R_2$, and magnification M. Other operating parameters, including x-ray exposure and x-ray focal spot size, were also analyzed in the simulations. Clinical conditions wherein the object 12 included a 50%-50% breast of 5 cm thickness, and an infiltrating ductal carcinoma lesion with a diameter and a thickness of 0.5 cm were assumed. This exemplary lesion represents a clinically relevant breast cancer-detection task, and the exemplary lesion-breast configuration kept appropriate signal-to-noise ratios (SNR) in the simulation for the conventional attenuation-based imaging. The parameters such as S(E), which is the normalized x-ray photon fluence spectrum, the image SNR and average glandular dose to the breast were derived from computer simulations. Also, no Bucky grid was assumed in the simulation because of the large air-gap involved in the phase-contrast x-ray imaging of the system 10 of the present invention.

Figure 2:
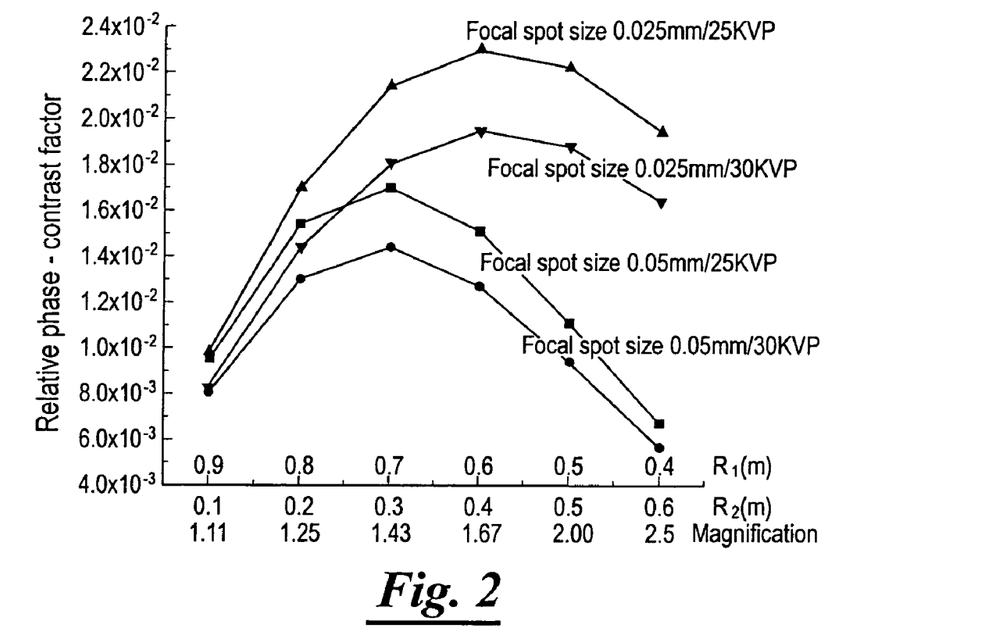
FIG. 2 is a graph showing phase visibility vs. system design parameters ($R_1$, $R_2$, and M). $R_1$ is the source to object distance, $R_2$ is the object to detector distance, and M is the magnification ratio. Two different exemplary focal spot sizes (0.025 mm and 0.05 mm) and two different exemplary x-ray energies (25 kVp and 30 kVp) were used.
Figure 3:
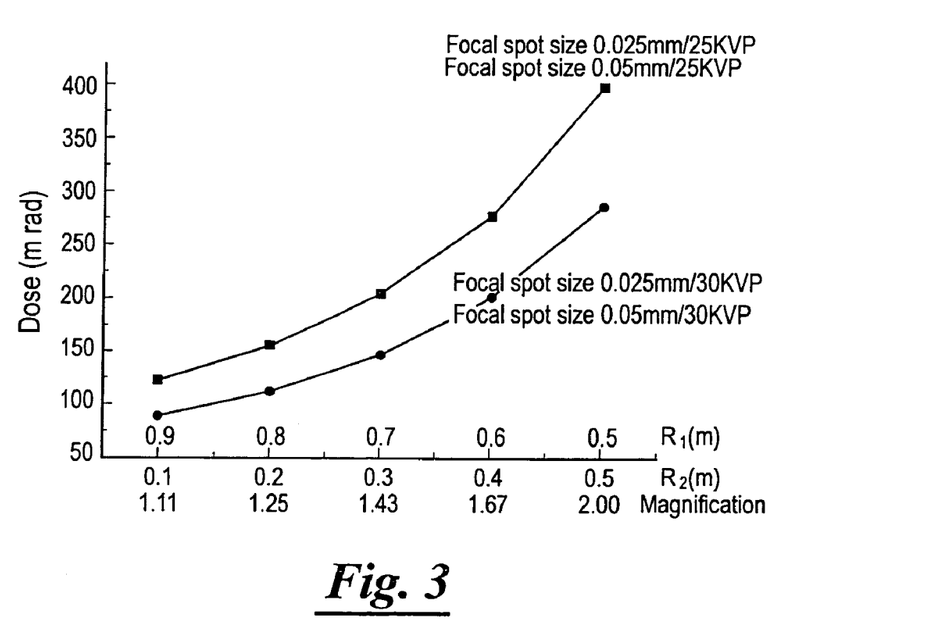
FIG. 3 is a graph showing x-ray dose vs. system design parameters ($R_1$, $R_2$, and M). $R_1$ is the source to object distance, $R_2$ is the object to detector distance, and M is the magnification ratio. Two different exemplary focal spot sizes (0.025 mm and 0.05 mm) and two different exemplary x-ray energies (25 kVp and 30 kVp) were used.

As shown in FIG. 2, the phase visibility increases with the object-to-detector distance $R_2$ and the magnification M. Based on the results in FIG. 2, the optimal phase visibility is achieved with a focal spot size of about 25 µm. As such, this focal spot size is preferred in one embodiment for the x-ray source 14. However, it should be understood that the present invention contemplates that other focal spot sizes can be used in accordance with the present invention, as discussed further below. Also, although the phase visibility results in FIG. 2 favor 25 kVp over 30 kVp, the results in FIG. 3 indicate that a higher x-ray dose would be required when a low x-ray energy is used.

Another consideration in designing the system is the object-to-detector distance $R_2$ and the source-to-object distance $R_1$. From the point view of Fresnel diffraction, $R_2$ cannot be too small, otherwise one would lose all of the phase information. This is because the diffracted beam has to travel sufficient lateral distance to be detected. Eq. (12) suggests that a large $R_2$ is favored for increasing imaged phase-contrast. However, if the magnification is controlled so as not to exceed two in accordance with current mammography practices, an increase of $R_2$ means an increase of $R_1$ as well. In one embodiment, considering a reasonable SID (Source to Image Receptor Distance), $R_2$ is set no larger than about 0.5 meter (m), and SID=($R_1$+$R_2$) is set to about 1 m. Furthermore, a large $R_2$ will reduce the scattering by the air gap effect. Thus, by using an air gap instead of a grid, the average glandular dose can be reduced.

Further, the focal spot size of the x-ray source should also be consider in designing the system 10. As is well known, the focal spot size is constrained by:

$$1/S \geq U\text{ob-max} (M-1)/M, \quad (16)$$

where $U_{ob-max}$ is the highest spatial frequency content desired to be imaged. Considering an exemplary task of detecting tiny microcalcifications in mammography, we assume $U_{ob-max}$=10 lp/mm. With a magnification of 2, the required focal spot size can be determined as S=200 µm. However, as is shown by Eq. (14), the smaller the focal spot, the larger the spatial coherence and the larger the phase-contrast visibility. However, a "point"-like x-ray source generally cannot provide a sufficiently high x-ray output to allow imaging to complete in a reasonable time period. Therefore, the system should balance the need of spatial coherence and a sufficient x-ray output flux.

To Applicants' knowledge, currently in mammography the minimal tube current which allows one to acquire a breast image in clinical settings with a reasonably short exposure time is about 25 mA. As a design trade-off, both 0.025 mm and 0.01 mm focal spots for 25 mA were considered by way of example. The 0.01 mm-focal spot provided a 10%-12% higher phase-contrast performance (in terms of RPF), as compared with the 0.025 mm focal spot. However, in the case of 0.01 mm spot, the electron-impact temperature of the anode increased by a factor of 3.95 as compared to the 0.025 mm focal spot, which would be too high for a Mo-target to withstand the 25 mA-tube current. In the case of 0.025 mm focal spot size for 25 mA, the tube loading is within the permissible range of current Mo-target. At the same time, the phase contrast is significant for the proposed clinical applications (the RPF is in the range of about 0.008 to 0.02). Therefore, about a 0.025 mm focal spot size is preferred for the system 10 of the present invention in one embodiment. However, it should be understood that other focal spot sizes may be utilized.

Phase-contrast imaging of an object such as breast tissue is based on the x-ray wave diffraction by the tissue. The x-ray attenuation of the tissue modulates the phase-contrast as well. In order to get a good phase-contrast image with a reasonable average glandular dose to the tissue, optimal target and filter choices should also be considered in designing the system 10.

In the diagnostic energy range of about 15-150 kiloelectron volt (keV), the phase-contrast varies with photon energy as 1/E, while the photoelectric absorption varies as $1/E^3$. As such, the x-ray spectral shape affects markedly the visibility of phase-contrast. Therefore, the previous optimization used for conventional mammography may not be valid for phase-contrast imaging.

In general, optimal spatial coherence can be achieved in x-ray imaging with a bright "point" x-ray source. However, a conventional point-like x-ray source cannot provide a sufficiently high x-ray output in order to acquire a clinical image in a reasonably short exposure time. Thus, the x-ray source 14 of the present invention is constructed so as to balance between the spatial coherence requirement and the x-ray output flux, while at the same time ensuring that the attenuation-based contrast will be well imaged and the radiation dose to subjected object 12 is kept below a desired limits, such as a limit falling within standard regulation limits in clinical applications.

In one embodiment of the present invention, the x-ray source 14 of the system 10 includes an x-ray tube (not shown). Preferably, the x-ray tube is designed so as to emit x-ray energy in the range of about 25 kilovolts peak (kVp) and about 30 kVp, or about 10 keV and about 160 keV. Further, the x-ray source 14 can be adapted to allow for different kVp settings for the system 10. In one embodiment, the x-ray tube is provided with a focal spot size in the range of about 0.001 millimeters (mm) to about 0.05 mm to about 0.20 mm. More preferably, the x-ray tube has a focal spot size of about 0.020 mm to about 0.030 mm, and more preferably of about 0.025 mm. Also, in one embodiment the x-ray tube has a tube current in the range of about 20 milliampers (mA) to about 40 mA, and preferably of about 25 mA. When imaging human breast tissue, the x-ray tube of the x-ray source 14 preferably has about a 0.025-mm focal spot size and about a 25-mA tube current.

The x-ray source 14 in one embodiment is a field-emission device (FED) which includes a field-emission cathode. In general, a FED is a micro-machined structure, usually with an array of sharp points, that emits electrons when a small electric potential is placed between the tip and an extraction electrode. The sharp tips enhance the field-emission effect since a relatively small voltage creates a large electric field at each point, allowing electrons to tunnel from the tip into the vacuum. The alternative is to heat the electrons with a hot filament until they have enough energy to jump over the barrier. However, conventional thermionic x-ray tubes or cathodes (i.e., heated filaments) with a micro-focus suffer from the space charge effect and generally cannot provide large enough tube current for clinical use (e.g., to produce 24-35 kVp).

On the other hand, field-emission cathodes use a large extraction electric field to emit electrons, which negates the space charges such that the space charge effect will not manifest until an extremely high current density as high as $10^9$ A/cm$^2$ is reached. Therefore, when the x-ray tube of the field emission cathode of the x-ray source 14 has a current density of for example 25 mA/25 micron, the current density is several magnitudes smaller than the $10^9$ A/cm$^2$ limit and will not suffer from the space charge problem.

Since the current density of the proposed x-ray tube (e.g., 25 mA/25 micron) is much higher than that encountered for conventional tubes, the cathode heating should also be address. In one embodiment, the field-emission cathode can be an electron gun made of a metallic nanocrystal material, which will allow a current density as high as $2 \times 10^7$ A/cm$^2$ without burning out. The nanocrystals preferably have a size of about 1 nanometer (nm) to about 2 nm. In each nanocrystal the translation symmetry is completely broken and electrons become zero-dimensional. The zero-dimensional material leads to diminished phonon generation, since the phase-space restrictions imposed by the strong quantum confinement inhibits phonon-induced carrier relaxation. However, the electrons tunnel from excited states to neighboring crystals more easily and fast. As such, the material composed from nanocrystals allows collective hopping of electrons by Coulomb interaction. This leads to a non-Ohmic electrical conduction with a negative temperature coefficient for the resistivity. These properties result in high field enhancement, beam confinement at the tip of the field emitter and high currents (e.g., with a current density of over $2\times10^7$ A/cm$^2$) without destroying the cathode.

The detector 18 of the system 10 is a device capable of collecting attenuation data and phase-contrast data. The detector 18 is preferably a digital device so as to allow for a computational application of the system 10. The detector 18 can also be a film cassette. In one embodiment, the detector 18 is a digital-conversion flat panel x-ray detector developed by Lorad-Hologic of Bedford, Mass. The Lorad-Hologic digital flat panel detector uses amorphous selenium with a thin film transistor (TFT) readout, and has a pixel pitch of 0.07 mm. In comparison with other commercial digital detectors (such as those developed by GE or Fischer), the Lorad-Hologic detector generally has a higher spatial resolution. The output of the Lorad-Hologic detector is essentially a digital image containing a plurality of pixels which are indicative of an intensity measurement across the detector surface (or detector plane). The digital images can be in any pixel format and bit-depth.

As can be seen, the system 10 preferably allows for phase-contrast imaging to be performed in different $R_1$ and $R_2$ settings. In one embodiment, to facilitate the positioning and alignment of the components of the system 10, the system 10 in one embodiment further includes a mechanical platform assembly 30 which extends longitudinally. At least one of the x-ray source 14, the object 12, or the detector 18 can be attached and selectively adjusted or translated along the longitude of the mechanical platform assembly 30. As such, the mechanical platform assembly 30 allows for the relative spacing between the x-ray source 14, the object 12, and/or the detector 18 (i.e., $R_1$ and/or $R_2$) to be readily adjustable within the system 10 while generally maintaining a longitudinal alignment therebetween.

The mechanical platform assembly 30 preferably includes at least one of a manually controlled translational slide (not shown) or a motorized translational platform (not shown), such as a motorized platform used for example in a LORAD M-IV mammography machine. Generally, a component of the system 10 which is expected to be minimally adjusted can be attached to a manual translational slide, while a component which is frequently adjusted or which will be automated or adjusted by a user via a computer system (such as the object-map generator 22) can be attached to a motorized translational platform. A component which is intended to remain stationary within the system 10 can be rigidly attached to the mechanical platform 30 directly or indirectly through an intermediate structure.

In one embodiment, the object 12 is releasably attached to the mechanical platform assembly 30 via an object support assembly 34 so that different objects can be readily placed in the system 10 for imaging. The object support assembly 34 can be any device which is adapted to receive and support the object 12 being imaged (e.g., a breast of a patient) so that the object 12 interacts with at least a portion of the x-rays generated by the x-ray source 14. The object support assembly 34 is preferably adjustable so as to provide flexibility in the size and shape of objects that can be received and supported by the object support assembly 34. Further, the object support assembly 34 is preferably attached to the mechanical platform assembly 30 so as to allow selective translation of the object support assembly 34 (and thus the object 12 being supported thereby) along the longitude of the mechanical platform assembly 30. Also, to offer more flexibility in the positioning of the object 12 within the system 10, the object support assembly 34 can be further adapted to allow translation of the object 12 being supported thereby in other directions, such one or more directions perpendicular to the longitude of the mechanical platform assembly 30.

In one embodiment, the object support assembly 34 includes a support 40 and a compression paddle 44 which attach to the mechanical platform and receive and support the object 12 (similar to that seen in prior art mammography systems). Preferably, the support 40 and the compression paddle 44 is slidably attached to the mechanical platform assembly 30 so that the relative distance between the support 40 and the compression paddle 44 can be readily adjusted so to accommodate the size and shape of the object 12, and so that the position of object 12 can be readily adjusted within the system 10.

While the support 40 and the compression paddle 44 of the object support assembly 34 are described in one embodiment as both being attached to the mechanical platform so that the relative distance between the support 40 and the compression paddle 44 can be adjusted, one skilled in the art would understand that alternatively the support 40 can be attached to the mechanical platform assembly 30, while the compression paddle 44 is adjustably attached to the support 40 (or vice versa) so as to allow adjustment of the relative distance between the support 40 and the compression paddle 44.

During an imaging procedure, the object 12 is preferably positioned first within the system 10. For example, when the object 12 is an extension of a human patient, the object 12 can positioned so as to provide comfort for the patient. To position the object 12 in the system 10, the object is placed between the support 40 and the compression paddle 44 of the object support assembly 34. Preferably, so that any portion of the object 12 or extension thereof (e.g., the patient) which is external to the system 10 does not have to move after the object 12 is placed in the system 10, the position of the object 12 is defined by first placing the support 40 in a desired position, placing the object 12 adjacent to the support 40, and then translating the compression paddle 44 adjacent to the object 12 so that the support 40 and the compression paddle 44 cooperate to appropriately receive and support the object 12. However, the position of the object 12 can also be defined by first placing the object 12 between the support 40 and the compression paddle 44 and then translating the support 40 and the compression paddle 44 (preferably simultaneously) so that the object 12 is placed in a desired position.

Once the object 12 is in position, the x-ray source 114 is adjusted to a desired $R_1$ distance from the object 14. In one embodiment, the distance between the x-ray source 14 and the object 12 (i.e., $R_1$) is in the range of about 0.4 meters and about 0.6 meters. The detector 18 is adjusted to a first desired $R_2$ distance from the object 12 to obtain the first image signal reading. The detector 18 is then moved to a second desired $R_2$ distance from the object 12 to acquire the second image signal reading. In one embodiment, the distance between the detector 18 and the object 12 (i.e., $R_2$) when the detector 18 is in the first position is about zero meters, and the distance between the detector 18 and the object 12 when the detector 18 is in the second position is in the range of about 0.3 meters and 0.6 meters. It should be noted that when a large air-gap exists between the object 12 and the detector 18, no Bucky grid is required.

Figure 4A:
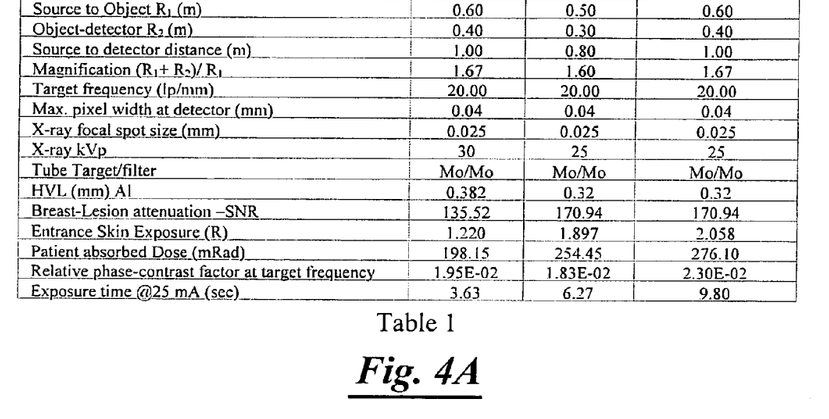
FIG. 4A shows a Table 1 providing various embodiments of the design parameters for the system shown in FIG. 1, wherein the system includes a screen-film based detector.
Figure 4B:
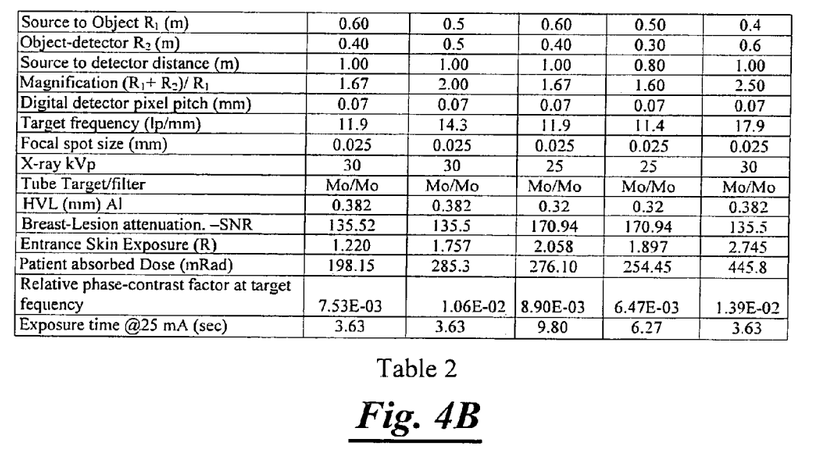
FIG. 4B shows a Table 2 providing various embodiments of the design parameters for the system shown in FIG. 1, wherein the system includes a digital based detector.

By way of illustration of various system designs and imaging arrangement, shown in FIG. 4A is a Table 1 for the system 10 with the detector 18 being a screen-film cassette, and shown in FIG. 4B is a Table 2 for the system 10 with the detector 18 being a digital detector, wherein each table shows three specific settings for imaging of an exemplary object which is a 0.5 cm-diameter infiltrating ductal carcinoma within a breast tissue of 5-cm thickness, with the expected relative phase-contrast factors. These parameters were derived through a computer simulation, based on the theory and formula discussed above.

The technical characteristics of the x-ray source 14, such as the focal spot size, as well as commonly used clinical mammography conditions, such as average glandular dose, were carefully observed in the simulation. The "target frequency" refers to the limiting spatial resolution of the system 10. The "relative phase-contrast factor" (RPF) indicates the contribution from phase-contrast to the visibility of the lesion, and the "breast-lesion attenuation SNR" represents the contribution from the attenuation-based contrast. Balancing the relative phase-contrast factor, lesion-attenuation based SNR, exposure time and the associated average glandular dose to the breast, an energy level of 30 kVp is preferred for phase-contrast imaging for the given lesion and breast thickness.

Note that the film based detector provided higher detector resolution, and thus a higher relative phase-contrast factor, than the digital detector. However, due to the capability of a wider dynamic range, and the impact of window-leveling in the image display of a digital detector, the effect of the edge enhancement from phase-contrast may be better visualized by human observers using digitally acquired images. Also, a detector pixel format can be selected for optimal phase-contrast x-ray imaging.

Figure 5:
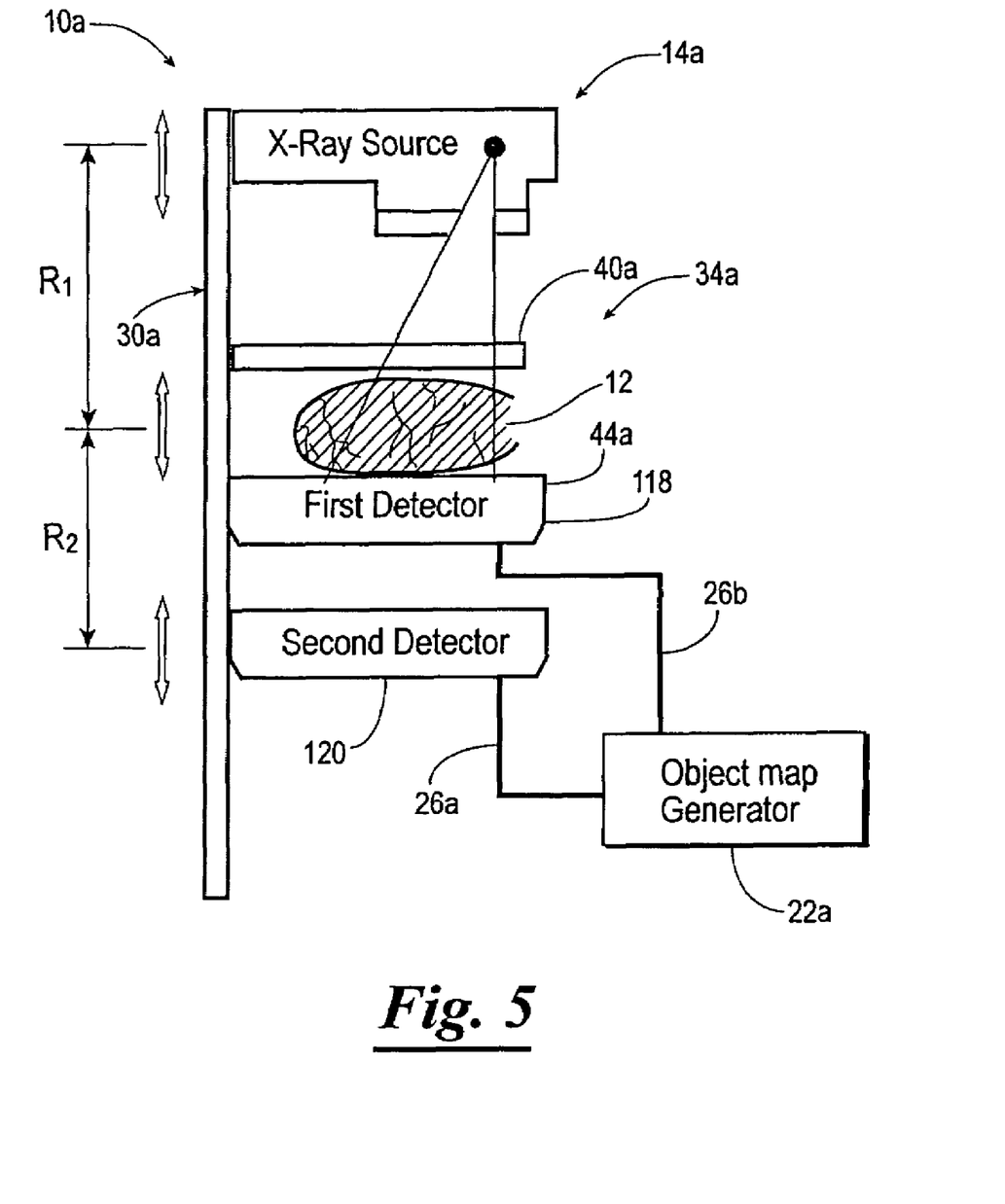
FIG. 5 is a schematic of one embodiment of another system for phase-contrast x-ray imaging of an object, which is constructed in accordance with the present invention.

Referring now to FIG. 5, shown therein and labeled by the reference numeral 10a is another embodiment of a system for phase-contrast imaging of the object 12, which is constructed in accordance with the present invention. The system 10a is similar to the system 10 discussed above with reference to FIG. 1 in that the system 10a includes an x-ray source 14a, an object-map generator 22a, a mechanical platform assembly 30a, and an object support assembly 34a (wherein similar components are denoted in FIG. 5 with the same reference numeral prefix, but with an added alphanumeric suffix). However, the system 10a shown in FIG. 5 differs from the system 10 shown in FIG. 1 in that the detector 18 of the system 10 is replaced in system 10a with a first detector 118 and a second detector 120 arrangement, the outputs of which are received by the object-map generator 22a via lines 26a and 26b, respectively. The output of the first detector 118 is preferably utilized to provide attenuation-based image information, while the output of the second detector 120 utilized to provide phase-contrast image information.

As discussed above, the system 10 utilizes two intensity readings acquired by the detector 18, one at about $R_2=0$ and one image at $R_2>0$. This function of acquiring two separate readings at two $R_2$ positions is performed in the system 10a shown in FIG. 5 by the first detector 118 and a second detector 120, with the first detector 118 being used to measure x-ray intensities at about $R_2=0$ and the second detector 120 being used to measure x-ray intensities at $R_2>0$. The first detector 118 is constructed so as to allow at least a portion of the x-rays to transmit through the first detector 118 to the second detector 120. As such, the dual detector approach of system 10a allows acquisition of the two image signals needed for phase-contrast imaging at one x-ray exposure. Using one x-ray exposure reduces the radiation dose and the opportunity for alignment errors, which may arise from moving the detector from $R_2=0$ to $R_2>0$ in between x-ray exposures during the imaging process.

Similar to the object support assembly 34 of system 10, the object support assembly 34a of system 10a in one embodiment includes a support 40a and a compression paddle 44a. Preferably, the support 40a is the first detector 118, as shown for example FIG. 5, when the first detector 118 is continually used to measure at $R_2=0$. In such an embodiment, the first detector 118 and the compression paddle 44a cooperate to receive and support the object 12, i.e., the object 12 is disposed between the compression paddle 44a and the first detector 118 so that the object 12 is positioned at a desired $R_1$ position. Since the first detector 118 is positioned directly adjacent the object 12, the $R_2$ object-to-detector distance for the first detector 118 is essentially $R_2=0$. The second detector 120 is then positioned a distance from the first detector 118. Thus, the $R_2$ object-to-detector distance for the second detector 118 will be $R_2>0$.

As discussed above, to allow at least a portion of the x-ray beams transmitted by the x-ray source 14a to be received by both the first detector 118 and the second detector 120 at one x-ray exposure, the first detector 118 is adapted so as to allow a portion of the x-ray beams to be transmitted therethrough to the second detector 120. When an x-ray beam is transmitted by the x-ray source 14a of the system 10a and passed through the object 12, a portion of the x-ray beam will be detected by the first detector 118 positioned directly adjacent the object 12. When the first detector 118 is a digital detector having a detector plate (not shown), the percentage of the x-ray beam that is detected by the first detector 118 depends on the quantum efficiency of a detector plate (not shown) of the first detector 118, which for example can be in the range of about 60-70%. The rest of the x-ray beam is typically attenuated by a backup material or housing material (not shown) which is disposed behind the detector plate (e.g., a cover, a circuit board, or wires). By carefully selecting the backup material (or removing a portion thereof), the attenuation can be minimized to about 5-10%. Thus, a portion of the original x-ray beam (about 20-30%) will exists after passing through the first detector 118, which can be detected by the second detector 120.

Because the first detector 118 is used in a manner similar to conventional attenuation based x-ray imaging detectors, most current detectors, for example mammography detectors, can be used to construct the first detector 118. However, as discussed above, the first detector 118 is preferably constructed to minimize the x-ray attenuation by materials behind the detector plate of the first detector 118 so that more x-ray photons can reach the second detector 120. For example, a fiber optically coupled CCD using a MinR screen generally absorbs about 65% of the incoming x-ray beam and the rest of the beam is basically 100% attenuated by the optical fibers that are attached with the screen. As such, the fiber optically coupled CCD using a MinR screen would likely not be suitable for constructing the first detector 118. Current flat panel detectors use either a semiconductor layer or a scintillating screen to detect x-ray photons, and allows about 30% of the incoming beam to be transmitted through the layers. However, electronic circuits and wires beneath the semiconductor layer attenuate these transmitted photons significantly. To decrease such interference, the circuits and/or wires can be made extremely thin and/or positioned mostly "sideways".

In one embodiment, the first detector 118 is constructed using a computed radiography (CR) plate (e.g., made of a photostimulable phosphor). For example, an FCR 5000 high resolution plate having a limiting resolution of about 10 lp/mm, made by Fuji Film, can be used to construct the first detector 188. For a high resolution CR-plate of $BaFBr_{0.85}I_{0.15}:Eu^{2+}$ phosphor with a coating weight of 40 mg/cm (using an exemplary x-ray beam from a Mo/Mo source at 30 kVp and a 50%-50% breast of about 5 cm), about 34% of the x-ray incident upon the CR-plate will transmit through the plate. Further, to minimize x-ray attenuation from the housing of the first detector 118, the housing can be constructed to have a thin carbon fiber back plate (instead of a metal back cover). With the additional attenuation of about 3% from the carbon fiber back plate, about 31% of the x-ray incident upon the first detector 118 will be transmitted and available for the second detector 120 to acquire the second image signal.

Because the second detector 120 is preferably used to record phase induced contrast, a high spatial resolution and high quantum efficiency is desired. A CR plate, as described above with reference to the first detector 118 can be used to construct the second detector 120. However, in a preferred embodiment, the second detector 120 is constructed using a digital flat panel detector developed by Lorad-Hologic, because of its higher quantum efficiency. As discussed above with reference to the detector 18 of the system 10 shown in FIG. 1, the Lorad-Hologic detector is a direct-conversion flat panel x-ray detector using amorphous selenium with a thin film transistor (TFT) readout, and can provide a 0.07 mm pixel pitch.

Although the dual-detector system 10a is described herein in one embodiment as the first detector 118 and the second detector 120 being digital detectors, the present invention contemplates that a modified screen-film cassette arrangement can also be used.

The same algorithms described above with reference to the single detector approach of the system 10, particularly Eqs. (9)-(12), can be also used for the dual detector approach of the system 10a when it is taken into consideration that for the dual detector case, the information of attenuation and phase acquired by the second detector 120 contains the contributions from the first detector 118 per se in addition to that from the object 12. The total attenuation and total phase sensed by the second detector 120 are related to that from the object 12 and the first detector 118 as:

$$A_{Total}^2 = A_{breast}^2 A_{D1}^2, \phi_{Total} = \phi_{breast} + \phi_{D1} \qquad (17)$$

where $A^2_{D1}$ and $\phi_{D1}$ are the attenuation and phase contributions of the first detector 118 to the measurement acquired by the second detector 120. If the first detector 118 (having for example a photostimulable phosphor CR-plate) were completely uniform, then $A^2_{D1}$ and $\phi_{D1}$ would contribute as two constants and their effects to the phase-map would require only minor resealing. However, the potential structural non-uniformity of the first detector 118 would make $A^2_{D1}$ and $\phi_{D1}$ non-uniform across the object 12. Therefore, in order to properly retrieve the object phase-map by using Eq. (11), $A^2_{D1}$ and $\phi_{D1}$ should be determined. This can be done during a calibration procedure by acquiring two measurements using the first detector 118 by itself (one at R2=0 another at R2>0), and applying Eq. (9) and (11).

Figure 6A:
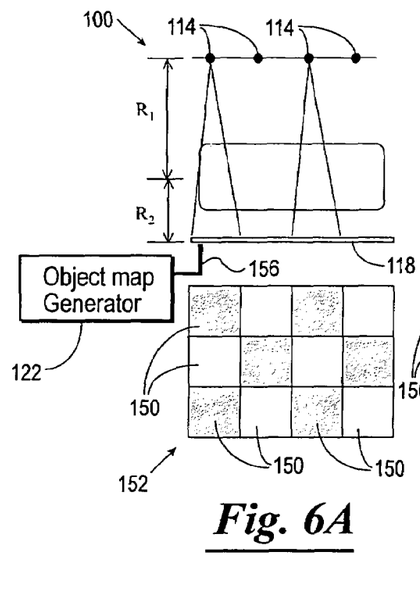
FIGS. 6A-6B are schematics of one embodiment of another system for phase-contrast x-ray imaging of an object, which is constructed in accordance with the present invention. The system, which is shown from a side view in FIGS. 6A-6B, has a plurality of x-rays sources providing two exposure patterns having alternating exposure areas, with one of the exposure patterns being shown from a top view below the system in FIG. 6A and the other exposure pattern being shown from a top view below the system in FIG. 6B (wherein the alternating exposure areas are shown darkened for purposes of illustration).
Figure 6B:
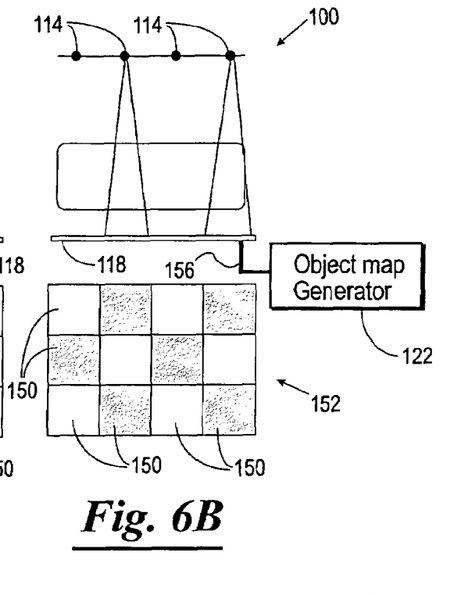

Referring now to FIGS. 6A-6B, shown therein and designated by a reference numeral 100 is a system for phase-contrast x-ray imaging of an object 12, which is constructed in accordance with the present invention. The system 100 includes a plurality of x-ray sources 114, at least one detector 118, and an object-map generator 122.

Each of the x-ray sources 114 of the system 100 is similar in construction and function to the x-ray source 14 of the system 10 discussed above with reference to FIG. 1, and therefore no further discussion is deemed necessary to teach one of ordinary skill in the art how to construct the individual x-ray sources 114 of the system 100. Each x-ray source 114 provides an exposure area 150 at the detector 118 where the x-rays generated by the x-ray source 114 are substantially projected (wherein only six exposure areas 150 are labeled in FIG. 6A-6B for purposes of clarity). Preferably, the plurality of x-ray sources 114 are arranged in an array formation so that the collective exposure areas 150 of the plurality of x-ray sources 114 define a combined exposure area 152 across the detector 18. For example, FIGS. 6A-6B shows the exposure areas 150 having a generally square shape, which results in the combined exposure area 152 having a substantially "checkerboard" pattern across the detector 118. In one embodiment, a collimator (not shown) is interposed between the plurality of x-ray sources 114 and the object 12 control the passage of the x-rays by the plurality of x-ray sources and produce the exposure areas 150.

Although the plurality of x-ray sources 114 are shown in FIG. 6a-6c by way of example as including twelve x-ray sources 114 arranged in a 4×3 checkerboard array, it should be understood that there can be any number of x-ray sources 114 arranged in different configurations in accordance with the present invention.

The at least one detector 118 of the multi-source system 100 is similar in construction and function as the detector 18 of the system 100 discussed above with reference to FIG. 1, and therefore no further discussion is deemed necessary to teach one of ordinary skill in the art how to construct the at least one detector 118 of the system 100. The at least one detector 118 is spaced a distance $(R_1+R_2)$ from the plurality of x-ray sources 114 so as to allow the object 12 to be positioned therebetween for imaging.

The object-map generator 122 of the multi-source system 100 is similar in construction and function as the object-map generator 22 of the system 100 discussed above with reference to FIG. 1. The object-map generator 122 of the system 100 receives via a line 156 the outputted image signals of the at least one detector 118 at detector positions of $R_2=0$ and $R_2>0$ in a similar manner as the object-map generator 22 of the system 10 to reconstruct or generate the attenuation-map and the phase-map of the object 12. However, in one embodiment, the object-map generator 122 of the system 100 utilizes a multi-step exposure process for imaging the object 12.

In the multi-step exposure process, only a portion of the x-ray sources 114 generate x-rays or are "fired" during each of the steps of the process, thus only projecting x-rays to a portion of the exposure areas 150 at the at least one detector 118 during that step. In other words, at least a portion of the x-ray sources 114 generate x-rays at a different time than another portion of the x-ray sources 114 such that the x-rays generated by each portion of the x-ray sources 114 interact with the object 12 and are received by the at least one detector 118 at different times. Preferably, once all the steps of the exposure process have been preformed, each x-ray source 118 will have been fired at least once, and thus overall, all the exposure areas 150 of the collective exposure area 152 will have been exposed to x-rays. The firing of the x-ray sources 114 and the clocking of the detectors 118 to sense the exposure can be controlled by either an open loop, e.g., where a timing technique is used for synchronization, or by a closed loop, e.g., where a signal from a first detector triggers a second x-ray source and detector 118, and so on. Generally, a simple timing technique is sufficient in providing control accuracy. Also, while the system 100 is described in one embodiment as using a multi-step exposure process in which the plurality of x-ray sources 314 are fired at different times, it should be understood that the partial image signals can also be generated by controlling the collimator to permit only the x-rays from certain x-ray sources 114 from being projected to the detector 118.

In the multi-step exposure embodiment, the object-map generator 122 of the system 100 collects the image signals outputted by the detector 118 during each step of the exposure process and assembles of superimposes the partial image signals to form a collective image signal. This is done when the detector 118 is positioned at $R_2=0$ and when the detector 118 is positioned at the $R_2>0$. The collective image signal at the $R_2=0$ position can then be used to generate an attenuation-map for the object 12 and the collective image signal at the $R_2>0$ position can be used to generate the phase-map for the object 12 using the algorithms discussed above with reference to the system 10. In one embodiment, during the multi-step exposure process, the plurality of x-ray sources 114 are fired in alternating sequences in a two-step process so as to produce two partial images having inverse checkerboard patterns, such as shown for example in FIGS. 6A-6B.

Figure 7:
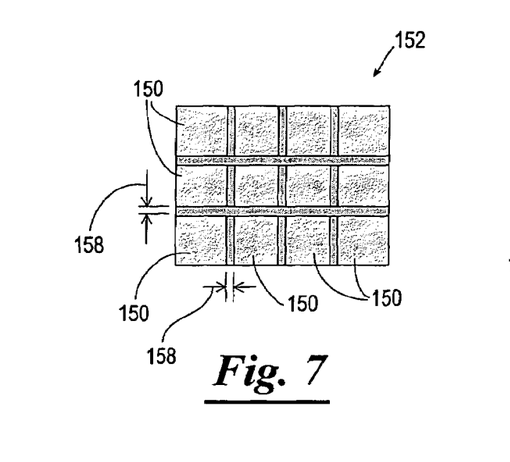
FIG. 7 is a top view of the combined exposure patterns depicted in FIGS. 6A-6B wherein adjacent exposure areas are provided with overlapping portions (wherein the overlapping portions are shown darkened for purposes of illustration).

In one embodiment, the plurality of x-ray sources 114 are further arranged such that at least a portion of each of the exposure areas 150 overlaps a portion of an adjacent exposure area 150 of another x-ray source 114, as shown best in FIG. 7 (wherein the ovalapping portions are shown darkened for purposes of illustration). Partially overlapping the exposure areas 150 reduces the possibility of having an un-exposed seam or gap in the final collective image signal after the partial image signals are recombined. Thus, it can be seen that the overlapping areas will be exposed at least twice during the exposure process. Assuming for example that the exposure areas 150 each have an area of about 714 mm$^2$ and the collective exposure area 152 has an effective area of about 43200 mm$^2$ (240 mm×180 mm), then a distance 158 measured between edges of two overlapping exposure areas 150 would be about 0.7 mm (which is equivalent to the length of about 10 pixels). In such an example, when compared to overall collective exposure area 152, the dose penalty to the object 12 due to the overlapped areas is only about 1.6%.

The multi-source system 100 of the present invention offers the following advantages. First, each x-ray source 114 can be built with very small focal spot size, therefore an essentially point source operation is achieved. Such a point source operation minimizes geometrical distortion, and allows use of a relatively short source-to-object distance ($R_1$), and a large object-to-detector distance ($R_2$) as preferred for optimal phase contrast x-ray imaging. Second, in the steps of the multi-step exposure process, the exposure area 150 of each x-ray source 114 can be set to a small size. This small exposure area 150 is separated from adjacent exposure areas 150 since the corresponding x-ray sources 114 are fired alternately in different steps of the exposure process. Such geometry leads to significantly reduced x-ray scatter, and therefore improves image contrast and/or reduces object (e.g., patient) radiation. Lastly, although each point-source can only provide limited photo flux, the multiple x-ray sources 114 provide sufficient photo flux as required by clinical procedures. Therefore, the present invention allows the exposure time and dose to the object 12 (e.g., patient) to be controlled to a reasonable amount.

In one preferred embodiment, when the multi-source system 100 is used for example in a phase-contrast mammography application, each of the plurality of x-ray sources 114 is a field emission x-ray tube having a focal spot size in the range of about 0.001 mm to about 0.05 mm. The source-to-object distance $R_1$ is in the range of about 50 mm to about 1000 mm. The object-to-detector distance $R_2$ is in the range of about 50 mm to about 1000 mm. The size of each exposure area 150 is in the range of about 10 cm×10 cm to about 100 cm×100 cm, and preferably is about 60 cm×60 cm. The distance between each x-ray source 114 is in the range of about 10 cm to about 100 cm, and preferably is about 60 cm. The size of the collective exposure area 152 is about 240 cm×180 cm or larger. Also, the overall height/width of the multi-source system 100 is preferably constructed so as to approximately equivalent to current mammography machines.

With the above design parameters, the multi-source system 100 can be used to acquire a full-field mammogram. Also, the multi-source system 100 can be used without a Bucky grid. Since a Bucky grid may cut about 30% primary radiation, the multi-source system 100 offers 30% dose reduction to the object 12 for the same image quality.

It should also be understood that the present invention contemplates that other features described herein with reference to the systems 10 and 10a can also be included in the system 100 (or modifications thereof). For example, the system 100 can further include at least one mechanical platform assembly and at least one object support assembly, which are similar in construction and function as the mechanical platform assemblies 30 and 30a and the object support assemblies 34 and 34a, as discussed above with reference to the systems 10 and 10a, respectively.

Figure 8:
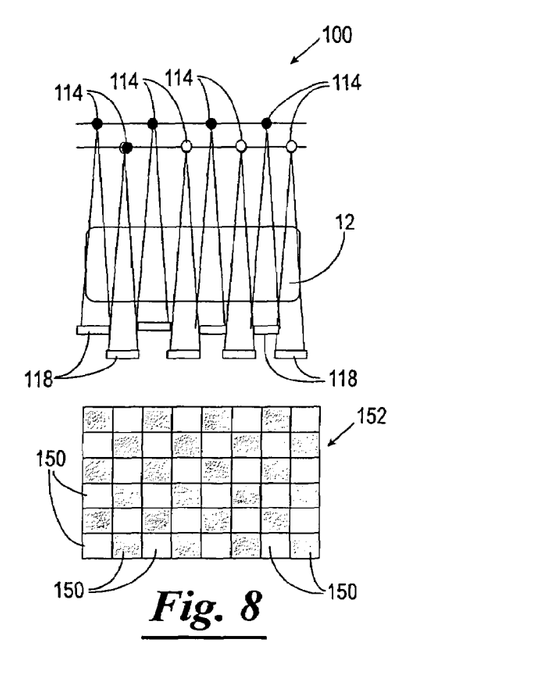
FIG. 8 is schematics of one embodiment of another system for phase-contrast x-ray imaging of an object, which is constructed in accordance with the present invention. The system, which is shown from a side view, is constructed using a mosaic source-detector approach with a plurality of x-rays sources (shown staggered for purposes of illustration) and a plurality of detectors (shown staggered for purposes of illustration). Shown below the system is a top view of a plurality of exposure areas provided by the plurality of x-ray sources at the plurality of x-ray detectors (wherein alternating exposure areas are shown darkened for purposes of illustration).

Also, while the at least one detector 118 is shown in FIGS. 6a-6b as one detector 118, it should be understood that any number of detectors 118 can be used in accordance in accordance with the present invention to collectively form a detector plane. For example, as shown in FIG. 8, the system 100 in one embodiment can include a plurality of detectors 118 corresponding to the plurality of x-ray sources 114 (only four detectors 118 and four x-ray sources being labeled in FIG. 8 for purposes of clarity), wherein each of the x-ray sources 114 projects its exposure area 150 substantially to its corresponding detector 118, thereby forming a "mosaic" source-detector arrangement (only six exposure areas 150 being labeled in FIG. 8 for purposes of clarity). The image signals from each of each of the plurality of detectors 118 can then be outputted to the object-map generator 122 of the system 100 which then combines or assembles the mosaic of partial image signals to generate a collective image signal.

Furthermore, while the system 100 has been described in one embodiment as utilizing a single-detector arrangement wherein the at least one detector 118 is used to acquire intensity measurements at the two positions $R_2=0$ and $R_2>0$ in a similar manner as discussed above with reference to system 10, it should be understood that the present invention contemplates that the system 100 can be modified so as to have dual-detector arrangement with at least one first detector is positioned at $R_2=0$ and at least one second detector is positioned at $R_2>0$, in a similar manner as discussed above with reference to system 10a (see FIG. 5). Also, it can be seen that when the "mosaic" source-detector arrangement is also utilized, there will be at least one of a plurality of first detectors or a plurality of second detectors.

As a general note, moving a detector (or detectors) between different $R_2$ positions will simplify the system design and lead to lower cost (by reducing the number of components). However it takes a longer time to acquire a complete image of an object, as well as leads to higher radiation to the object being imaged. Thus, the single-detector approach of the present invention is more appropriate for phantom imaging or other procedures where time and radiation are not significant considerations. For most clinical (or patient related) applications, the dual-detector approach of the present invention is more practical, even with the higher system expenses.

From the above description, it is clear that the present invention is well adapted to carry out the objects and to attain the advantages mentioned herein, as well as those inherent in the invention. Although the foregoing invention has been described in some detail by way of illustration and example for purposes of clarity of understanding, it will be apparent to those skilled in the art that certain changes and modifications may be practiced without departing from the spirit and scope of the present invention, as described herein. As such, those skilled in the art will appreciate that the conception upon which this disclosure is based may readily be utilized as a basis for the designing of other structures, methods, and systems for carrying out the several purposes of the present invention. As such, it should be understood that the invention is not limited to the specific and preferred embodiments described herein, including the details of construction and the arrangements of the components as set forth in the above description or illustrated in the drawings. Further, it should be understood that the phraseology and terminology employed herein are for the purpose of description and should not be regarded as limiting.

What is claimed is:

1. A system for phase-contrast x-ray imaging for imaging an object, comprising:
   an x-ray source generating x-rays, at least a portion of the x-rays interacting with the object;
       a detector positioned to receive the x-rays generated by the x-ray source after at least a portion of the x-rays have interacted with the object and output an image signal indicative of the intensity of the x-rays received, the detector being movable between a first position and a second position; and
   an object-map generator receiving the image signal output by the detector when the detector is in the first position and the image signal output by the detector when the detector is in the second position, the object-map generator utilizing the first position image signal and the second position image signal to generate an attenuation-map and a phase-map for the object.

2. The system of claim 1, wherein the x-ray source comprises a field emission device.

3. The system of claim 2, wherein the field emission device has a focal spot size of in the range of about 0.001 millimeters to 0.20 millimeters.

4. The system of claim 3, wherein the field emission device has a focal spot size of about 0.025 mm.

5. The system of claim 2, wherein the field emission device emits x-ray energy in the range of about 25 kVp to 30 kVp.

6. The system of claim 1, wherein the object-map generator utilizes the attenuation-map and a phase-map to generate an object-map for the object.

7. The system of claim 1, further comprising an object support assembly adapted to receive and support the object such that the object interacts with at least a portion of the x-rays generated by the x-ray source.

8. The system of claim 1, wherein the system further includes a mechanical platform assembly, and wherein at least one of the x-ray source, the object support assembly, or the detector is connected to the mechanical platform assembly so that at least one of the distances between the x-ray source, the support assembly, and the detector is adjustable.

9. The system of claim 1, wherein the distance between the x-ray source and the object is in the range of about 0.4 meters to 0.6 meters.

10. The system of claim 1, wherein the distance between the detector and the object when the detector is in the first position is zero meters, and the distance between the detector and the object when the detector is in the second position is in the range of about 0.3 meters to 0.6 meters.

11. A system for phase-contrast x-ray imaging for imaging an object, comprising:
    an x-ray source generating x-rays, at least a portion of the x-rays interacting with the object;
    a first detector positioned at a first position to receive the x-rays generated by the x-ray source after at least a portion of the x-rays have interacted with the object and output an image signal indicative of the intensity of the x-rays received, the first detector being constructed so as to allow transmission of at least a portion of the x-rays through the first detector;
    a second detector positioned at a second position to receive the x-rays transmitted through the first detector and output an image signal indicative of the intensity of the x-rays received; and
    an object-map generator receiving the image signal from the first detector and the image signal from the second detector, the object-map generator utilizing the image signal from the first detector and the image signal from the second detector to generate an attenuation-map and a phase-map for the object.

12. The system of claim 11, wherein the x-ray source comprises a field emission device.

13. The system of claim 12, wherein the field emission device has a focal spot size in the range of about 0.001 millimeters to about 0.20 millimeters.

14. The system of claim 13, wherein the field emission device has a focal spot size of about 0.025 mm.

15. The system of claim 12, wherein the field emission device emits x-ray energy in the range of about 25 kVp to 30 kVp.

16. The system of claim 11, wherein the object-map generator utilizes the attenuation-map and a phase-map to generate an object-map for the object.

17. The system of claim 11, further comprising an object support assembly adapted to receive and support the object such that the object interacts with at least a portion of the x-rays generated by the x-ray source.

18. The system of claim 11, wherein the system further includes a mechanical platform assembly, and wherein at least one of the x-ray source, the object support assembly, the first detector or the second detector is connected to the mechanical platform assembly so that at least one of the distances between the x-ray source, the support assembly, the first detector and the second detector is adjustable.

19. The system of claim 11, wherein the distance between the x-ray source and the object is in the range of about 0.4 meters to 0.6 meters.

20. The system of claim 11, wherein the distance between the first detector and the object is zero meters.

21. The system of claim 11, wherein the distance between the second detector and the object is in the range of about 0.3 meters and 0.6 meters.

22. A system for phase-contrast x-ray imaging for imaging an object, comprising:
    a plurality of x-ray sources generating x-rays, at least a portion of the x-rays generated by the plurality of x-ray sources interacting with the object;
    at least one detector positioned to receive at least a portion of the x-rays generated by the plurality of x-ray sources and output an image signal indicative of the intensity of the x-rays received, the at least one detector being movable between a first position and a second position;
    an object-map generator receiving a plurality of image signals from the at least one detector when the at least one detector is in the first position and a plurality of image signals from the at least one detector when the at least one detector is in the second position, the object-map generator combining the plurality of image signals associated with the first position to form a collective image signal for the first position and combining the plurality of image signals associated with the second position to form a collective image signal for the second position, the object-map generator further utilizing the collective image signal for the first position and the collective image signal for the second position to generate an attenuation-map and a phase-map for the object.

23. The system of claim 22, wherein at least a portion of the x-ray sources generate x-rays at a different time than another portion of the x-ray sources such that the x-rays generated by each portion of the x-ray sources interact with the object and are received by the at least one detector at different times.

24. The system of claim 22, further comprising a collimator disposed between the plurality of x-ray sources and the detector, the collimator controlling the transmission of the x-rays from the plurality of x-ray sources such that the x-rays generated by a portion of the x-ray sources interact with the object and are received by the at least one detector at a different time than another portion of the x-ray sources.

25. The system of claim 22, wherein the plurality of x-ray sources are disposed in an array formation such that each x-ray source provides an exposure area at the at least one detector where the x-rays of the x-ray source are substantially projected.

26. The system of claim 25, wherein the exposure area of each x-ray source has a generally square shape, and the exposure areas of the plurality of x-ray sources provides a substantially checkerboard exposure pattern across the at least one detector.

27. The system of claim 26, wherein the plurality of x-ray sources comprises a first group of x-ray sources and a second group of x-ray sources, the first group of x-ray sources and the second group of x-ray sources including alternating x-ray sources in the array formation, the first group of x-ray sources generating x-rays at a different time then the second group of x-ray sources so as to form two exposure patterns at the detector, each of the exposure patterns having alternating areas with x-ray exposure and areas without x-ray exposure.

28. The system of claim 26, further comprising a collimator disposed between the plurality of x-ray sources and the detector, the collimator controlling the transmission of the x-rays generated by a first group of x-ray sources and a second group of x-ray sources, the first group of x-ray sources and the second group of x-ray sources including alternating x-ray sources in the array formation, the collimator controlling the transmission of the x-rays generated by the first group of x-ray sources and the second group of x-ray sources such that the x-rays generated by the first group of x-ray sources interact with the object and are received by the at least one detector at a different time than the x-rays generated by the second group of x-ray sources so as to form two exposure patterns at the detector, each of the exposure patterns having alternating areas with x-ray exposure and areas without x-ray exposure.

29. A system for phase-contrast x-ray imaging for imaging an object, comprising:
  a plurality of x-ray sources generating x-rays, at least a portion of the x-rays generated by the plurality of x-ray sources interacting with the object;
  at least one first detector positioned at a first position to receive at least a portion of the x-rays generated by the plurality of x-ray sources after at least a portion of the x-rays have interacted with the object and output an image signal indicative of the intensity of the x-rays received, the at least one first detector being constructed so as to allow transmission of at least a portion of the x-rays through the at least one first detector;
  at least one second detector positioned at a second position to receive the x-rays transmitted through the at least one first detector and output an image signal indicative of the intensity of the x-rays received;
  and;
  an object-map generator receiving a plurality of image signals from the at least one first detector for the first position and a plurality of image signals from the at least one second detector for the second position, the object-map generator combining the plurality of image signals associated with the first position to form a collective image signal for the first position and combining the plurality of image signals associated with the second position to form a collective image signal for the second position, the object-map generator further utilizing the collective image signal for the first position and the collective image signal for the second position to generate an attenuation-map and a phase-map for the object.

* * * * *

UNITED STATES PATENT AND TRADEMARK OFFICE
CERTIFICATE OF CORRECTION

PATENT NO. : 7,412,026 B2 Page 1 of 1
APPLICATION NO. : 11/171006
DATED : August 12, 2008
INVENTOR(S) : Hong Liu and Xizeng Wu It is certified that error appears in the above-identified patent and that said Letters Patent is hereby corrected as shown below:

On the Title Page:
Under (73) Assignee: After "The Board of Regents of the University of Oklahoma, Norman, OK (US)" insert the Assignee -- The UAB Research Foundation, Birmingham, AL (US) --.

In the Specification:
Column 15, line 44: After "minor" delete "resealing" and replace with -- rescaling --

In the Claims:
Column 19, line 36: After "spot size" delete "of".

Signed and Sealed this

Twenty-first Day of October, 2008

JON W. DUDAS
*Director of the United States Patent and Trademark Office*